United States Patent
Pressacco

(10) Patent No.: US 8,864,826 B2
(45) Date of Patent: Oct. 21, 2014

(54) INTEGRATED PROSTHETIC ELEMENT

(75) Inventor: Michele Pressacco, Udine (IT)

(73) Assignee: Limacorporate SpA, San Daniele del Friuli (IT)

( * ) Notice: Subject to any disclaimer, the term of this patent is extended or adjusted under 35 U.S.C. 154(b) by 8 days.

(21) Appl. No.: 13/581,005

(22) PCT Filed: Feb. 25, 2011

(86) PCT No.: PCT/IB2011/000407
§ 371 (c)(1),
(2), (4) Date: Sep. 18, 2012

(87) PCT Pub. No.: WO2011/138646
PCT Pub. Date: Nov. 10, 2011

(65) Prior Publication Data
US 2013/0006354 A1  Jan. 3, 2013

(30) Foreign Application Priority Data

Feb. 26, 2010 (IT) ................. UD2010A0037

(51) Int. Cl.
*A61F 2/02* (2006.01)
*A61F 2/30* (2006.01)

(52) U.S. Cl.
CPC ........... *A61F 2/30* (2013.01); *A61F 2002/3092* (2013.01); *A61F 2310/00029* (2013.01); *A61F 2310/00023* (2013.01); *A61F 2210/0071* (2013.01); *A61F 2002/30772* (2013.01); *A61F 2002/30065* (2013.01); *A61F 2002/30971* (2013.01); *A61F 2/3094* (2013.01); *A61F 2002/30985* (2013.01); *A61F 2310/00131* (2013.01)
USPC ...................................... 623/11.11

(58) Field of Classification Search
CPC ........... A61F 2/4601; A61F 2002/2846; A61F 2002/2839; A61F 2002/30011; A61F 2002/30013; A61F 2002/30028; A61F 2002/30029; A61F 2002/30138; A61F 2002/30942; A61F 2002/30985

USPC .......... 623/23.72–23.76, 11.11, 22.32, 22.33, 623/23.29, 23.3, 23.5–23.61, 20.14–20.36
See application file for complete search history.

(56) References Cited

U.S. PATENT DOCUMENTS 3,848,273 A * 11/1974 Frey ............................ 623/23.29
3,852,045 A * 12/1974 Wheeler et al. ............... 428/566

(Continued)

FOREIGN PATENT DOCUMENTS

EP        1683593       7/2006
WO     2006/078662    7/2006

OTHER PUBLICATIONS

International Search Report dated Jun. 29, 2011 filed in PCT/IB2011/000407.

*Primary Examiner* — Alvin Stewart

(74) *Attorney, Agent, or Firm* — Rankin, Hill & Clark LLP

(57) ABSTRACT

Integrated prosthetic element usable for bone implant operations or as a bone filler or replacement, comprising at least a metal support and an insert made of plastic material coupled with at least a first surface of said metal support so as to define a wear surface, or insert, of adjustable thickness. The metal support comprises, on the side opposite said first surface, a second surface intended to be coupled with the bone part on which the prosthesis or bone replacement is installed. The first surface comprises a layer having cavities or holes distributed in a substantially uniform manner and suitable for anchorage and solidarization of the plastic material that makes up the insert, while said second surface comprises a porous layer suitable to optimize the bone anchorage. The first surface and the second surface are separated by a compact layer that stops the plastic material in the step of forming the plastic insert. The cavities or holes of the first surface have bigger shapes and sizes than, and in any case different from, the pores of the second surface.

8 Claims, 6 Drawing Sheets

(56) References Cited

U.S. PATENT DOCUMENTS

| | | | | |
|---|---|---|---|---|
| 3,855,638 A * | 12/1974 | Pilliar | | 623/23.55 |
| 4,542,539 A * | 9/1985 | Rowe et al. | | 623/23.57 |
| 4,570,271 A * | 2/1986 | Sump | | 128/898 |
| 4,595,393 A * | 6/1986 | Anapliotis et al. | | 623/23.33 |
| 4,608,052 A * | 8/1986 | Van Kampen et al. | | 623/23.29 |
| 4,756,862 A * | 7/1988 | Spector et al. | | 264/126 |
| 4,955,911 A * | 9/1990 | Frey et al. | | 623/23.51 |
| 4,976,738 A * | 12/1990 | Frey et al. | | 623/23.54 |
| 4,978,355 A * | 12/1990 | Frey et al. | | 623/23.54 |
| 4,978,358 A * | 12/1990 | Bobyn | | 623/23.34 |
| 5,015,817 A * | 5/1991 | Kranz | | 219/121.14 |
| 5,021,063 A * | 6/1991 | Tager | | 623/23.33 |
| 5,108,435 A * | 4/1992 | Gustavson et al. | | 623/23.53 |
| 5,141,521 A * | 8/1992 | Wenner | | 623/23.34 |
| 5,226,917 A * | 7/1993 | Schryver | | 623/22.37 |
| 5,282,861 A * | 2/1994 | Kaplan | | 623/23.51 |
| 5,433,750 A * | 7/1995 | Gradinger et al. | | 623/23.54 |
| 5,439,744 A * | 8/1995 | Claar et al. | | 428/408 |
| 5,441,537 A * | 8/1995 | Kenna | | 419/2 |
| 5,443,510 A * | 8/1995 | Shetty et al. | | 419/2 |
| 5,455,100 A * | 10/1995 | White | | 428/131 |
| 5,491,882 A * | 2/1996 | Walston et al. | | 29/419.1 |
| 5,522,894 A * | 6/1996 | Draenert | | 623/23.61 |
| 5,564,064 A * | 10/1996 | Martin | | 419/5 |
| 5,732,469 A * | 3/1998 | Hamamoto et al. | | 29/896.6 |
| 5,869,170 A * | 2/1999 | Cima et al. | | 428/304.4 |
| 5,876,452 A * | 3/1999 | Athanasiou et al. | | 623/23.72 |
| 5,879,398 A * | 3/1999 | Swarts et al. | | 623/22.21 |
| 6,010,336 A * | 1/2000 | Shimotoso et al. | | 433/201.1 |
| 6,013,853 A * | 1/2000 | Athanasiou et al. | | 424/423 |
| 6,051,117 A * | 4/2000 | Novak et al. | | 204/252 |
| 6,087,553 A * | 7/2000 | Cohen et al. | | 623/22.21 |
| 6,187,329 B1 * | 2/2001 | Agrawal et al. | | 424/426 |
| 6,206,924 B1 * | 3/2001 | Timm | | 623/17.16 |
| 6,296,667 B1 * | 10/2001 | Johnson et al. | | 623/23.61 |
| 6,306,424 B1 * | 10/2001 | Vyakarnam et al. | | 424/426 |
| 6,309,595 B1 * | 10/2001 | Rosenberg et al. | | 420/417 |
| 6,312,473 B1 * | 11/2001 | Oshida | | 623/23.55 |
| 6,379,816 B1 * | 4/2002 | De Loose et al. | | 428/608 |
| 6,454,811 B1 * | 9/2002 | Sherwood et al. | | 623/23.76 |
| 6,592,787 B2 * | 7/2003 | Pickrell et al. | | 264/44 |
| 6,626,950 B2 * | 9/2003 | Brown et al. | | 623/23.72 |
| 6,660,224 B2 * | 12/2003 | Lefebvre et al. | | 419/2 |
| 6,682,567 B1 * | 1/2004 | Schroeder | | 623/22.24 |
| 6,797,007 B1 * | 9/2004 | Von Chamier et al. | | 623/22.45 |
| 6,840,960 B2 * | 1/2005 | Bubb | | 623/23.5 |
| 6,858,042 B2 * | 2/2005 | Nadler et al. | | 623/11.11 |
| 6,974,625 B2 * | 12/2005 | Hunter et al. | | 428/304.4 |
| 6,976,999 B2 * | 12/2005 | Charlebois et al. | | 623/16.11 |
| 7,001,672 B2 * | 2/2006 | Justin et al. | | 428/615 |
| 7,052,710 B2 * | 5/2006 | Giordano et al. | | 424/423 |
| 7,122,057 B2 * | 10/2006 | Beam et al. | | 623/23.51 |
| 7,186,364 B2 * | 3/2007 | King et al. | | 264/241 |
| 7,208,222 B2 * | 4/2007 | Rolfe et al. | | 428/304.4 |
| 7,235,107 B2 * | 6/2007 | Evans et al. | | 623/23.51 |
| 7,241,313 B2 * | 7/2007 | Unwin et al. | | 623/17.11 |
| 7,537,664 B2 * | 5/2009 | O'Neill et al. | | 148/525 |
| 7,578,851 B2 * | 8/2009 | Dong et al. | | 623/22.21 |
| 7,597,715 B2 * | 10/2009 | Brown et al. | | 623/22.32 |
| 7,648,735 B2 * | 1/2010 | Hunter et al. | | 427/248.1 |
| 7,674,426 B2 * | 3/2010 | Grohowski, Jr. | | 419/2 |
| 7,682,540 B2 * | 3/2010 | Boyan et al. | | 264/212 |
| 7,722,735 B2 * | 5/2010 | Bulko | | 156/249 |
| 7,740,795 B2 * | 6/2010 | Wang et al. | | 419/2 |
| 7,758,643 B2 * | 7/2010 | Stone et al. | | 623/14.12 |
| 7,794,828 B1 * | 9/2010 | Momoda et al. | | 428/307.7 |
| 7,815,826 B2 * | 10/2010 | Serdy et al. | | 264/49 |
| 7,819,925 B2 * | 10/2010 | King et al. | | 623/23.58 |
| 7,833,278 B2 * | 11/2010 | Evans et al. | | 623/23.51 |
| 7,883,653 B2 * | 2/2011 | Smith et al. | | 264/248 |
| 7,887,598 B2 * | 2/2011 | Evans et al. | | 623/23.51 |
| 7,892,291 B2 * | 2/2011 | Evans et al. | | 623/23.51 |
| 7,938,861 B2 * | 5/2011 | King et al. | | 623/18.11 |
| 8,080,483 B2 * | 12/2011 | Hillhouse et al. | | 438/780 |
| 8,197,550 B2 * | 6/2012 | Brown et al. | | 623/22.32 |
| 8,268,100 B2 * | 9/2012 | O'Neill et al. | | 148/525 |
| 8,268,383 B2 * | 9/2012 | Langhorn | | 427/2.26 |
| 8,287,915 B2 * | 10/2012 | Clineff et al. | | 424/602 |
| 8,292,967 B2 * | 10/2012 | Brown et al. | | 623/23.19 |
| 8,298,292 B2 * | 10/2012 | Swords et al. | | 623/23.72 |
| 8,361,150 B2 * | 1/2013 | Zhang et al. | | 623/17.11 |
| 8,398,720 B2 * | 3/2013 | Swords | | 623/23.55 |
| 8,470,042 B2 * | 6/2013 | Zhang et al. | | 623/17.11 |
| 8,518,433 B2 * | 8/2013 | Kizer et al. | | 424/426 |
| 8,556,972 B2 * | 10/2013 | Gordon et al. | | 623/16.11 |
| 8,556,981 B2 * | 10/2013 | Jones et al. | | 623/20.17 |
| 2001/0053937 A1 * | 12/2001 | Johnson et al. | | 623/23.34 |
| 2003/0173459 A1 * | 9/2003 | Fanucci et al. | | 244/123 |
| 2003/0220696 A1 * | 11/2003 | Levine et al. | | 623/17.17 |
| 2004/0034419 A1 * | 2/2004 | Carter et al. | | 623/14.12 |
| 2004/0193270 A1 * | 9/2004 | DiMauro et al. | | 623/17.11 |
| 2004/0210316 A1 * | 10/2004 | King et al. | | 623/18.11 |
| 2004/0220672 A1 * | 11/2004 | Shadduck | | 623/17.16 |
| 2005/0015088 A1 * | 1/2005 | Ringeisen | | 606/69 |
| 2005/0027366 A1 * | 2/2005 | Saini et al. | | 623/23.5 |
| 2005/0049715 A1 * | 3/2005 | Ito et al. | | 623/23.5 |
| 2005/0085817 A1 * | 4/2005 | Ringeisen | | 606/69 |
| 2005/0102036 A1 * | 5/2005 | Bartee et al. | | 623/23.76 |
| 2005/0112397 A1 * | 5/2005 | Rolfe et al. | | 428/593 |
| 2005/0187638 A1 * | 8/2005 | Glien et al. | | 623/23.56 |
| 2005/0251268 A1 * | 11/2005 | Truncale | | 623/23.63 |
| 2006/0040507 A1 * | 2/2006 | Mak et al. | | 438/758 |
| 2006/0084282 A1 * | 4/2006 | Dubois et al. | | 438/781 |
| 2006/0178748 A1 * | 8/2006 | Dinger et al. | | 623/18.11 |
| 2006/0178749 A1 * | 8/2006 | Pendleton et al. | | 623/20.15 |
| 2006/0224244 A1 * | 10/2006 | Thomas et al. | | 623/20.28 |
| 2006/0235542 A1 * | 10/2006 | Hodorek et al. | | 623/23.51 |
| 2006/0293760 A1 * | 12/2006 | DeDeyne | | 623/23.76 |
| 2007/0116734 A1 * | 5/2007 | Akash | | 424/423 |
| 2007/0141854 A1 * | 6/2007 | Chao et al. | | 438/758 |
| 2007/0150068 A1 * | 6/2007 | Dong et al. | | 623/22.32 |
| 2007/0191962 A1 * | 8/2007 | Jones et al. | | 623/22.32 |
| 2007/0233135 A1 * | 10/2007 | Gil et al. | | 606/86 |
| 2007/0233264 A1 * | 10/2007 | Nycz et al. | | 623/18.11 |
| 2007/0276506 A1 * | 11/2007 | Troxel | | 623/23.63 |
| 2008/0071381 A1 * | 3/2008 | Buscher et al. | | 623/18.11 |
| 2009/0017096 A1 * | 1/2009 | Lowman et al. | | 424/426 |
| 2009/0024223 A1 * | 1/2009 | Chen et al. | | 623/23.63 |
| 2009/0024224 A1 * | 1/2009 | Chen et al. | | 623/23.72 |
| 2009/0024229 A1 * | 1/2009 | Chen et al. | | 623/23.73 |
| 2009/0043398 A1 * | 2/2009 | Yakimicki et al. | | 623/23.51 |
| 2009/0084491 A1 | 4/2009 | Uthgenannt | | |
| 2009/0112315 A1 * | 4/2009 | Fang et al. | | 623/11.11 |
| 2009/0132047 A1 * | 5/2009 | Mansmann et al. | | 623/14.12 |
| 2009/0143867 A1 * | 6/2009 | Gage et al. | | 623/23.72 |
| 2009/0162235 A1 * | 6/2009 | Kita et al. | | 419/2 |
| 2009/0192610 A1 * | 7/2009 | Case et al. | | 623/16.11 |
| 2009/0220561 A1 * | 9/2009 | Jin et al. | | 424/423 |
| 2009/0326674 A1 * | 12/2009 | Liu et al. | | 623/23.55 |
| 2010/0047309 A1 * | 2/2010 | Lu et al. | | 424/423 |
| 2010/0075419 A1 * | 3/2010 | Inagaki et al. | | 435/402 |
| 2010/0100123 A1 * | 4/2010 | Bennett | | 606/213 |
| 2010/0137990 A1 * | 6/2010 | Apatsidis et al. | | 623/17.16 |
| 2010/0222892 A1 * | 9/2010 | Linares | | 623/23.5 |
| 2010/0254900 A1 * | 10/2010 | Campbell et al. | | 424/1.65 |
| 2010/0256758 A1 * | 10/2010 | Gordon et al. | | 623/16.11 |
| 2010/0268337 A1 * | 10/2010 | Gordon et al. | | 623/16.11 |
| 2010/0286795 A1 * | 11/2010 | Stone et al. | | 623/23.72 |
| 2010/0291178 A1 * | 11/2010 | Lu et al. | | 424/423 |
| 2010/0292791 A1 * | 11/2010 | Lu et al. | | 623/13.12 |
| 2011/0014081 A1 * | 1/2011 | Jones et al. | | 419/2 |
| 2011/0014289 A1 * | 1/2011 | Datta et al. | | 424/486 |
| 2011/0022180 A1 * | 1/2011 | Melkent et al. | | 623/23.5 |
| 2011/0022181 A1 * | 1/2011 | Kasahara et al. | | 623/23.5 |
| 2011/0054482 A1 * | 3/2011 | Truckai et al. | | 606/94 |
| 2011/0098818 A1 * | 4/2011 | Brodke et al. | | 623/17.11 |
| 2011/0125284 A1 * | 5/2011 | Gabbrielli et al. | | 623/23.4 |
| 2011/0153028 A1 * | 6/2011 | Albertorio | | 623/23.53 |
| 2011/0172798 A1 * | 7/2011 | Staiger et al. | | 700/98 |
| 2011/0224791 A1 * | 9/2011 | Hodorek et al. | | 623/14.12 |
| 2011/0244010 A1 * | 10/2011 | Doshi | | 424/402 |
| 2011/0257753 A1 * | 10/2011 | Gordon et al. | | 623/18.11 |
| 2011/0278533 A1 * | 11/2011 | Hillhouse et al. | | 257/9 |
| 2011/0282392 A1 * | 11/2011 | Murphy et al. | | 606/279 |

(56) References Cited

U.S. PATENT DOCUMENTS

| | | | |
|---|---|---|---|
| 2011/0287167 A1* | 11/2011 | Wei et al. | 427/2.1 |
| 2012/0022662 A1* | 1/2012 | Conway et al. | 623/22.21 |
| 2012/0046752 A1* | 2/2012 | Blanchard et al. | 623/18.11 |
| 2012/0076733 A1* | 3/2012 | Chernomorsky et al. | 424/9.3 |
| 2012/0101592 A1* | 4/2012 | Thomas et al. | 623/23.55 |
| 2012/0150299 A1* | 6/2012 | Ergun et al. | 623/17.11 |
| 2012/0207808 A1* | 8/2012 | Evans et al. | 424/426 |
| 2012/0209396 A1* | 8/2012 | Myung et al. | 623/22.11 |
| 2012/0213911 A1* | 8/2012 | Bucciotti et al. | 427/2.26 |
| 2012/0253474 A1* | 10/2012 | Klein et al. | 623/23.76 |
| 2012/0277152 A1* | 11/2012 | Ringeisen et al. | 514/8.8 |
| 2012/0288537 A1* | 11/2012 | Schwendeman et al. | 424/400 |
| 2012/0294902 A1* | 11/2012 | Stupp et al. | 424/400 |
| 2013/0006354 A1* | 1/2013 | Pressacco | 623/11.11 |
| 2013/0030528 A1* | 1/2013 | Chen et al. | 623/14.12 |
| 2013/0030531 A1* | 1/2013 | Brodke et al. | 623/17.16 |
| 2013/0053938 A1* | 2/2013 | Miller et al. | 623/1.1 |
| 2013/0103076 A1* | 4/2013 | Montanari et al. | 606/213 |
| 2013/0116792 A1* | 5/2013 | Zhang et al. | 623/17.16 |
| 2013/0118377 A1* | 5/2013 | Hamman et al. | 106/122 |
| 2013/0131699 A1* | 5/2013 | Jiang et al. | 606/151 |
| 2013/0177467 A1* | 7/2013 | Gupta | 419/2 |
| 2013/0178947 A1* | 7/2013 | Monaghan et al. | 623/23.55 |
| 2013/0180970 A1* | 7/2013 | Vargas et al. | 219/137 |
| 2013/0190889 A1* | 7/2013 | Li et al. | 623/23.11 |
| 2013/0202672 A1* | 8/2013 | Wan et al. | 424/422 |
| 2013/0204384 A1* | 8/2013 | Hensley et al. | 623/20.35 |
| 2013/0211533 A1* | 8/2013 | Fonte et al. | 623/22.4 |
| 2013/0231750 A1* | 9/2013 | Taylor | 623/22.21 |
| 2013/0306484 A1* | 11/2013 | Bandyopadhyay et al. | 205/148 |
| 2013/0310908 A1* | 11/2013 | Omenetto et al. | 607/114 |
| 2013/0310948 A1* | 11/2013 | Luscher | 623/23.58 |

* cited by examiner

INTEGRATED PROSTHETIC ELEMENT

FIELD OF THE INVENTION

The present invention concerns an integrated prosthetic element for applications in prostheses and bone replacements.

More precisely, the present invention concerns an integrated prosthetic element and the relative method of production, which can be used for the restoration of animal articulations, more specifically, human articulations.

The invention is applied in the medical field of implants of bone prostheses and bone replacements.

BACKGROUND OF THE INVENTION

Prostheses are known, which are applied in parts of the human or animal body, normally made essentially by a metal support or shell to which an insert made of plastic material is coupled solidly, which facilitates the sliding of the mobile part of the prosthesis, thus allowing it to move and reducing wear on the parts.

The choice of material for the metal support and the plastic material of the insert is dictated by the use of bio-compatible materials; generally the metal support is made of pure titanium, titanium alloys, tantalum alloys, cobalt alloys, whereas the plastic material is for example high molecular weight polyethylene, polycarbonate urethane, polyether ether ketone or similar materials.

It is known to make at least the external surface of the metal support with a porous structure, the function of which is to allow the bone to bind after an implant operation, thus promoting the process of progressive osteo-integration of the prosthetic element.

The porous structure, if it is also present on the internal surface, or part of it, not only allows the osteo-integration process but can also be used to facilitate the solidarization of a wear insert made of plastic material.

One of the methods used to make the porous structure is DMSLS (Direct Metal Selective Laser Sintering). This method allows to make products and components of metal material with a solidification process of successive layers, with a predefined thickness, of powders of metal material, using laser beams. Another technique is EBM (Electron Beam Melting), which allows to make components, for example of titanium, starting from a bath of titanium powders, by means of a melting process in conditions of high vacuum, and solidification of successive layers as in the DMSLS technique.

In known solutions, the insert is normally made in advance already in the form it will have to have once made solid with the prosthetic element, and then attached to it during the course of the implant operation, or already prepared in advance.

In order to allow the plastic insert to be made solid with the metal support, a known solution provides that the plastic insert, already pre-formed, is heated until a pre-established level of softness is reached, and subsequently the two parts, plastic and metal, are made solid with each other by pressing, in this way making one part of the surface of the plastic material penetrate, in a controlled manner, into the pores of the metal element.

One disadvantage of this solution is that it is necessary to control carefully the level of heating and of penetration of the plastic insert into the metal support, because the pores must not be completely filled since these are required for the process of osteo-integration after the implant.

Another disadvantage of this type of prosthetic element is that it is necessary to make the plastic insert in advance in the desired form, which entails additional operations, and also reduces the possibility of keeping in store a series of inserts of a suitable shape and size.

U.S. Pat. No. B1-6,682,567 describes a prosthetic component having an external surface suitable for osteo-integration and an internal polymer lining. The prosthetic component, in the solution described, is obtained in ceramic material, starting from a green body that is lined on the inner side and the outer side by a porous layer, and then sintered in the furnace.

On the inside of the ceramic body the internal polymer lining is then injected. Incidentally, U.S. '567 hypothesizes using any metal substance to make the shell, for example titanium. The method to make the porous titanium shell is not described.

US 2009/0084491 A1 describes another solution in which a porous layer is applied, for example glued or welded, on a metal base, and then the polymer layer is attached on the porous layer.

One purpose of the present invention is to make a prosthetic element of the type indicated above, that is easier to make, avoiding complex preparation operations and limiting the times and costs of production.

Another purpose of the present invention is to avoid operations of pre-forming the plastic insert before it is made solid with the support structure, and to avoid having to manage stocks in store.

Another purpose of the present invention is to achieve a more stable and resistant union of the metal material and the plastic material.

Another purpose of the present invention is to allow to make integrated prosthetic elements with a more limited thickness compared with state-of-the-art integrated prosthetic elements.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, an integrated prosthetic element according to the present invention can be used for bone implant operations as a prosthesis for the femur, shoulder, knee and so on. The prosthetic element is also applicable as a bone filler or replacement, insert, shell or suchlike.

The integrated prosthetic element according to the invention comprises at least a metal support and an insert made of plastic material, coupled with at least a first surface of the metal support so as to define a wear surface, or insert, with a thickness adjustable as desired.

On the side opposite the first surface, the metal support comprises a second surface intended for coupling with the bone part on which the prosthesis or bone replacement is installed.

According to the present invention, the first surface comprises cavities or holes distributed in a substantially uniform manner and suitable for the anchorage and solidarization of the plastic material that makes up the insert, whereas the second surface comprises a layer or porous structure suitable to optimize the anchorage of the bone, in which the first surface and the second surface are separated by a compact layer that stops the plastic material in the casting step to form the plastic insert, and in which the cavities or holes of the first surface have bigger shapes and sizes than, and in any case different from, the pores of the second surface.

To give an example, the sizes of the pores in the bone anchoring layer vary in a range from about 250 to about 1000 μm, whereas the size in width of the holes and cavities in the solidarization layer of the plastic material varies from 1200 to 2500 μm and more, according to the overall sizes of the prosthetic element.

The plastic insert is at least partly obtained by feeding plastic material in a liquid or semi-liquid state into the cavities or holes of the solidarization layer made in the first surface.

The compact layer contains the liquid plastic material when it is being fed, preventing it from penetrating and being dispersed on the opposite surface of the metal support.

By solidarization layer we mean any structure which has surface holes or apertures that extend inside and create at least undercuts, or which has a series of open cavities intercommunicating and connected to each other, or which allows to anchor the plastic insert and make it solid with the metal support layer.

The insert is obtained by feeding the plastic material in its liquid or semi-liquid state, firstly until the cavities or holes of the solidarization layer are completely filled, and then by feeding further material so as to form, on the side where the plastic material is fed, outside said solidarization layer, a protruding insert with the desired shape and size. The shape and size of the integrated prosthetic element is coherent on each occasion with the type of application.

The metal support is advantageously made of titanium and/or cobalt and/or tantalum and/or alloys thereof The plastic insert is made of a polymer material, advantageously chosen from a group comprising polyethylene, polycarbonate urethane, polyether ether ketone.

In this case it is advantageous to use polyether ether ketone and polycarbonate urethane because after melting these materials have a viscosity suitable to facilitate the casting process into the porous structure.

The present invention also concerns a method for the production of the integrated prosthetic element.

The method comprises a first step in which the metal support is made, which has at least a first surface and a second surface separated by a compact layer, in which cavities or holes are made on the first surface so as to define a solidarization layer, whereas there is a surface porosity on the second surface, and a second step of feeding, casting or injecting plastic material in the liquid or semi-liquid state, which penetrates into the cavities or holes of the solidarization layer until it reaches the compact layer, in which the holes or cavities extend inside and create at least undercuts, or are open cavities intercommunicating and connected to each other, and in which the metal support and the relative first and second surface are made in a single process using the EBM (Electron Beam Melting) technique.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF SOME PREFERENTIAL FORMS OF

Embodiment

Figure 1:
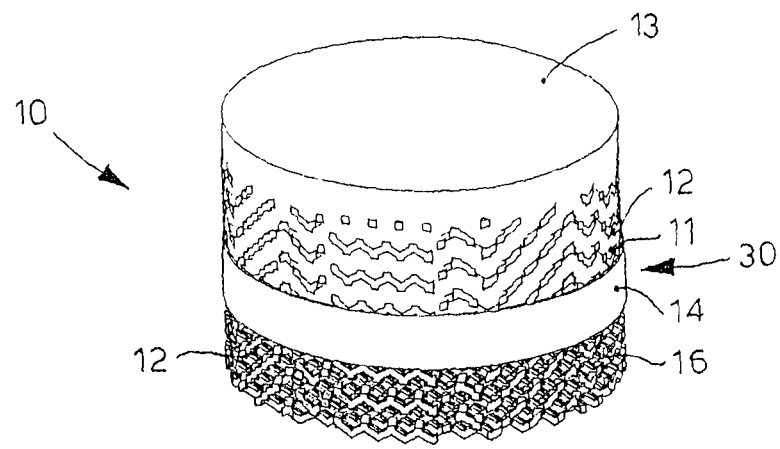
FIG. 1 is a three-dimensional view of a first configuration of the integrated prosthetic element according to the present invention.

In the drawings to which reference will be made for the description of some forms of embodiment, the functional parts that perform the same functions have the same reference numbers. In particular, an integrated prosthetic element according to the present invention is denoted in its entirety by the reference number 10.

With reference to FIG. 1 a first simplified form of embodiment of the integrated prosthetic element 10 is shown.

The integrated prosthetic element 10 in FIG. 1 comprises a metal support 30 and a plastic insert 13 made solid in said metal support 30.

The metal support 30 comprises a first surface, for example internal, defining a first layer or solidarization layer 11 of the plastic insert 13; in a position directly adjacent to the solidarization layer 11 there is a compact layer 14.

Figure 11A:
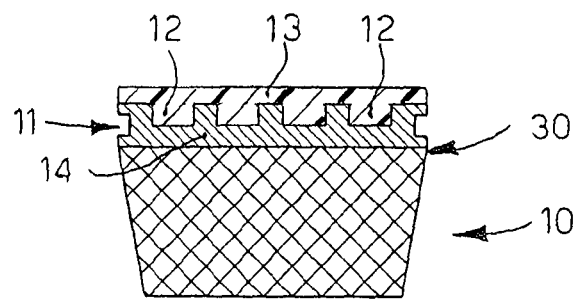
Figure 11B:
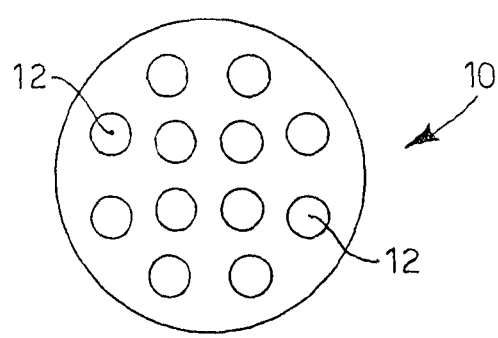
Figure 11C:
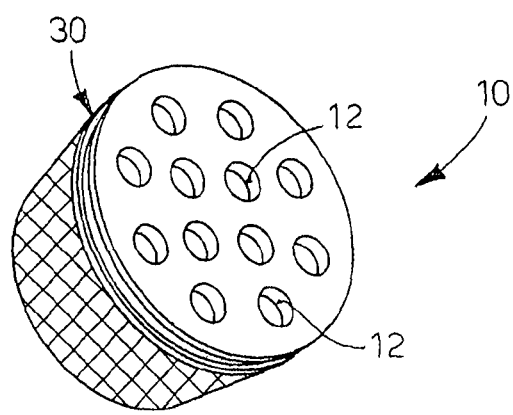

The solidarization layer 11 has blind holes and/or cavities 12 on the surface which extend internally and are intercommunicating with each other. An example of this configuration is shown in FIGS. 11a-11c.

Figure 9A:
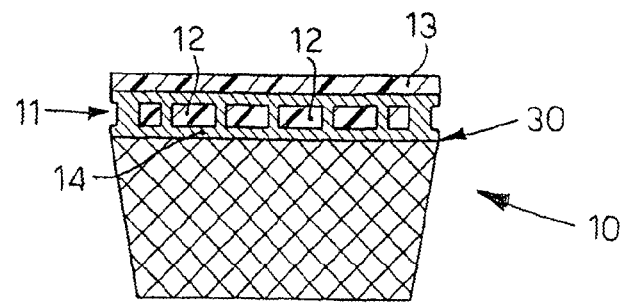
FIGS. 9a-9c, 10a-10c and 11a-11c show, respectively in section, in plane and in perspective view, other forms of embodiment of the prosthetic element according to the present invention, where in the plane view and the perspective view the layer of plastic material has been omitted, for clarity of illustration.
Figure 9B:
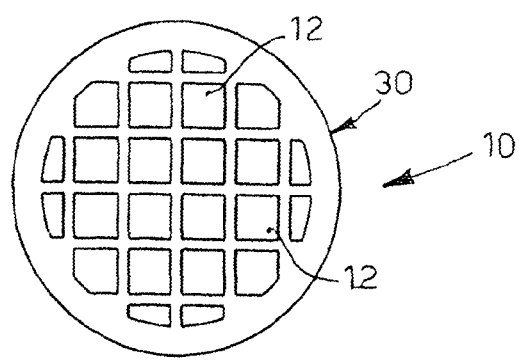
Figure 9C:
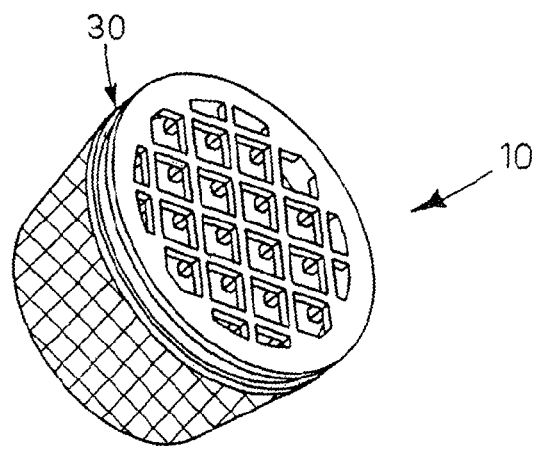
Figure 10A:
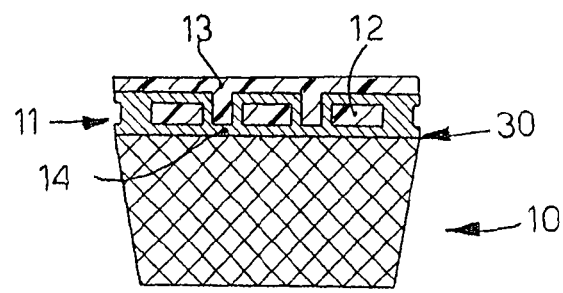
Figure 10B:
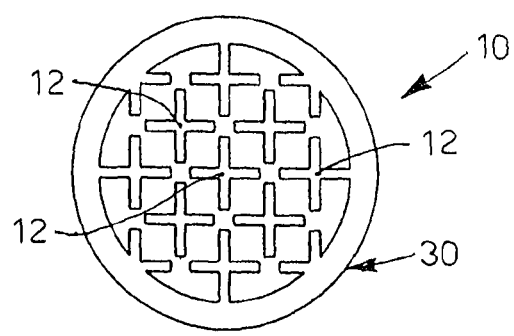

In other forms of embodiment the solidarization layer 11 can comprise binding structures, such as for example nets with a regular mesh, such as a grid (FIGS. 9a-9c) or cross (FIGS. 10a-10c), connected to each other, in proximity to the interconnections, with vertical elements, the whole being attached to the compact layer 14.

The holes or cavities 12 have relatively big widths, which can vary from 1200 to 2500 mm and more.

Other forms of embodiment of the solidarization layer 11 comprise surfaces having conical holes with axes extending inside the support, inclined with respect to each other, or not.

Figure 7:
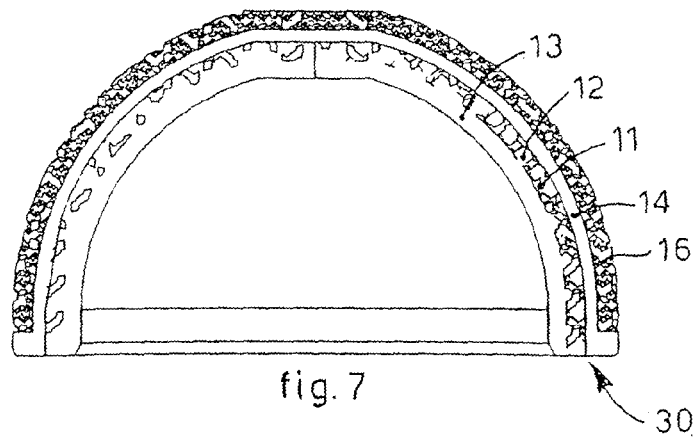
Figure 10C:
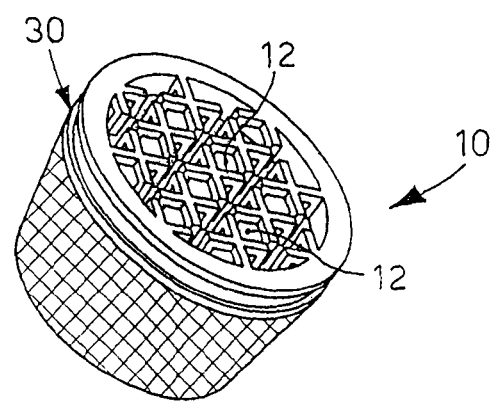

In other forms of embodiment, the solidarization layer 11 consists of "spider"-type structures, which are attached solidly, in proximity to their feet, to the compact layer 14, as with reference to FIG. 7 and FIG. 10c.

If the plastic insert 13 is made on irregular surfaces that have curved shapes in general, the solidarization layer 11 may consist of holes 12 with a circular or square section, or any other shape, with a regular extension perpendicular to the surface where the holes are made. An example of this form of embodiment is shown in FIGS. 11a, 11b and 11c where in this case the holes 12 have a circular section so that a mesh is generated, supported by pylons able to create interstices between the surfaces and to allow the insert 13, once solidified, to remain firmly attached to the metal support 30.

According to other forms of embodiment of the present invention, the holes 12 with a circular, square section or any other shape are interconnected so as to define binding elements.

In yet other forms of embodiment the holes 12 are not interconnected.

It is understood that any form whatsoever of cavity structure, or alternative structures, that allow to solidarize the plastic material of the insert 13, after it has been cast and cooled, is to be considered comprised within the field of the present invention.

In the case shown in FIG. 1, as we said, the solidarization layer 11 has cavities 12 which are filled with plastic material cast in the liquid or semi-liquid state, and the plastic material is then contained by the compact layer 14. Continuing to cast the plastic material 13, a plastic insert 13 is formed, with a desired height or thickness and closely interconnected to the solidarization layer 11.

It is clear that, in this description, we use the term "layer" for convenience to indicate the compact layer 14 and the solidarization layer 11 of metal material; however, this does not mean that they are two separate layers later joined, but the same body having parts with different morphological properties (compact material on one side, porous structure on the other).

The solidarization layer 11 and the compact layer 14 are made solid with a material based on pure titanium, or an alloy thereof, or cobalt alloys, tantalum alloys and/or alloys thereof, or any other biocompatible alloy.

The plastic material must also have biocompatible properties, good properties of mechanical resistance, resistance to wear and chemical-physical properties such as to facilitate injection inside a porous structure which, to give a non-restrictive example, may be made of polymer material, advantageously chosen from a group comprising polyethylene, polycarbonate urethane, polyether ether ketone or suchlike.

In this case it is advantageous to use polyether ether ketone and polycarbonate urethane, since these materials, after melting, have a viscosity suitable to facilitate the casting process into the solidarization layer 11 of the metal support 30.

On the surface or opposite side, the prosthetic element 10 has a second layer or porous layer 16, made contiguous to the compact support layer 14.

The porous layer 16 is able to promote the osteo-integration of the whole prosthetic element 10 in the bone, so that pores are made on it, or even micro-pores, which over time ensure an efficient hold of the element 10 on the bone.

The presence of the compact layer 14 that acts as a stop element for the cast plastic material that forms the insert 13 guarantees that the porosity of the porous layer 16 is not compromised by the plastic material.

The porous layer 16 normally has pores of smaller shape and sizes than the holes and cavities 12 of the solidarization layer 11, since the former are intended for osteo-integration and the second are intended for anchoring the plastic material that forms the insert 13.

In particular, the pores of the porous layer 16 can vary in a range of about 250 to about 1000 μm.

One characteristic of the present invention is that the metal support 30, with its solidarization 11, compact 14 and porous 16 layers, is obtained by the Electron Beam Melting Technique, or EBM, described in more detail hereafter.

This technique ensures that it is possible to obtain the desired geometric and dimensional characteristics, with extreme precision, both in terms of undercuts and blind cavities for the solidarization layer 11, and in terms of pores and micro-holes for the porous layer 16, and also in terms of height and density of the compact layer 14.

Figure 2:
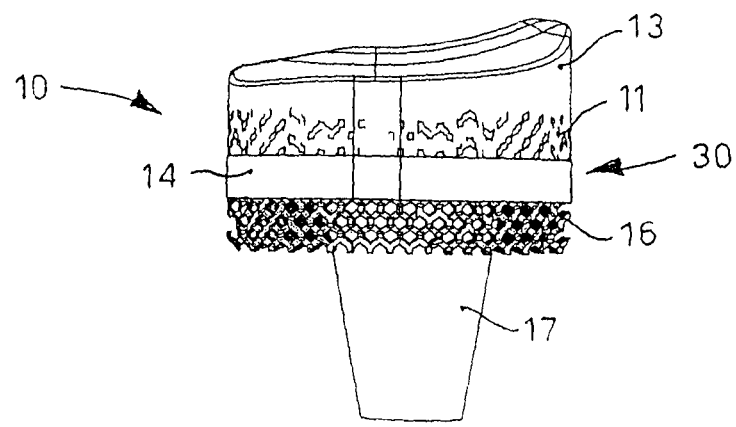
FIGS. 2 and 3 show views, respectively lateral and three-dimensional, of alternative forms of embodiment of the invention.
Figure 3:
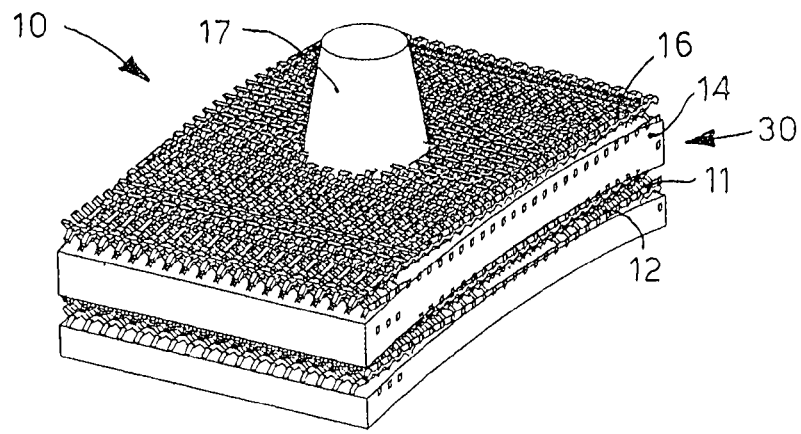

FIGS. 2 and 3 show two alternative forms of embodiment of the integrated prosthetic element 10 according to the invention, which show that the shapes of the integrated prosthetic element 10 can be different depending on the type of application required.

In particular, these solutions show an attachment pin 17 made of compact metal material, made solid with the compact layer 14 and through through the second porous layer 16.

The pin 17 serves to attach the whole integrated prosthetic element 10 in the bone and, according to the applications, can be integrated with further attachment elements not shown in the drawings.

In these cases, FIG. 2 shows a tibia insert while FIG. 3 shows a glenoid insert.

Figure 4:
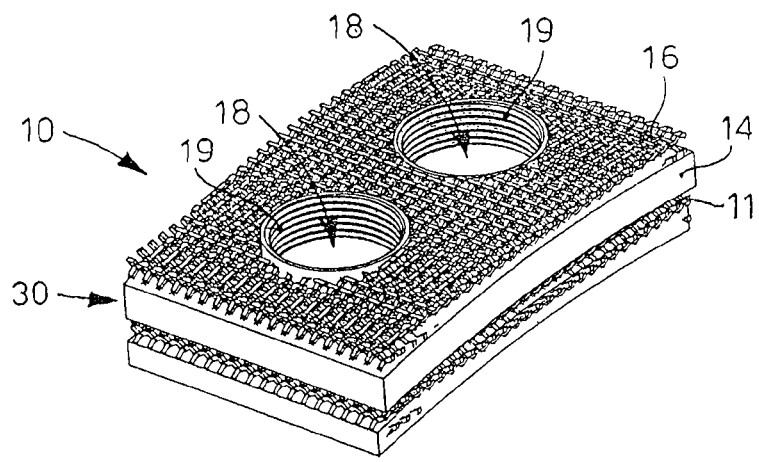
FIG. 4 shows a three-dimensional view of an integrated prosthetic element that has through holes for the attachment of the prosthetic element to the bone.

FIG. 4 shows a variant in which the integrated prosthetic element 10 comprises through holes 18 which allow to attach it to the bone wall in which the implant will be made; the through holes 18 are each delimited by an annular wall 19 made of compact material to strengthen the constraining hole 18 and to allow screws (not shown in the drawing) to be inserted.

Figure 5:
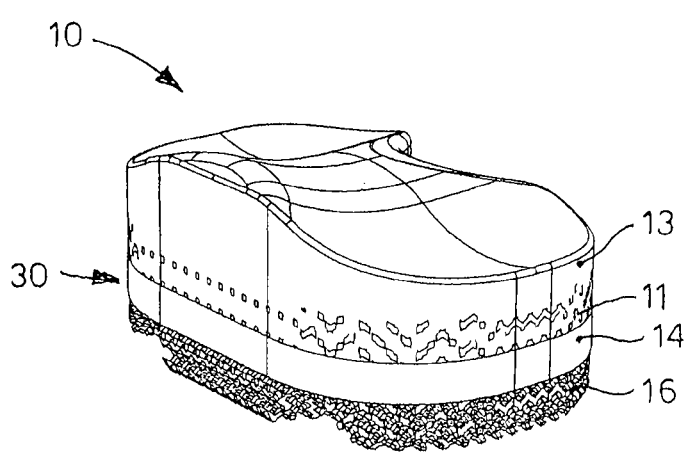
FIG. 5 is a three-dimensional view of another form of embodiment of the invention.

FIG. 5 shows another alternative form of embodiment, in which the tibia insert in FIG. 2 does not have the attachment pin 17 and the plastic insert 13 is made with a geometric shape suitable to conform and allow the sliding of a knee joint.

Figure 6:
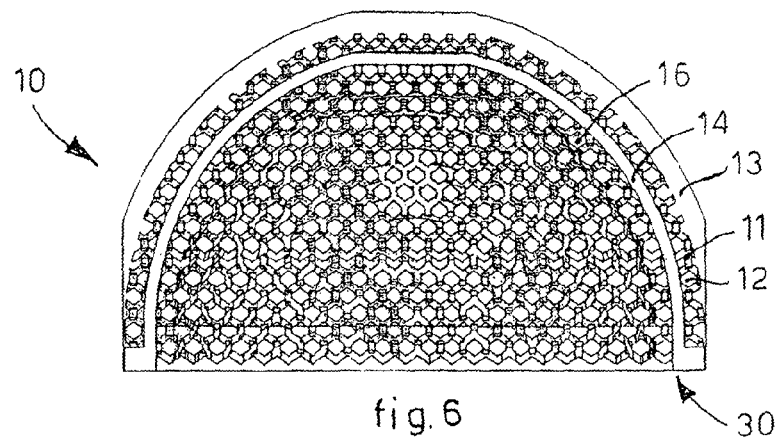
FIGS. 6 and 7 are section views respectively of a femoral head and an acetabular cup according to the present invention.

FIG. 6 shows an example of the application of the integrated prosthetic element 10 according to the present invention to a prosthesis for the head of the femur; a prosthetic element of similar shape and the same conformation may be applied in a prosthesis of a humeral head.

FIG. 7 shows an example of the application of the integrated prosthetic element 10 to an acetabular cup.

The method to make the integrated prosthetic element comprises a step of making the metal support 30 and a step of feeding the plastic material in a liquid or semi-liquid state.

The metal support 30 is made, as we said, using the technique known as EBM (Electron Beam Melting).

This technique provides to melt, in conditions of high vacuum and with an apparatus suitable for EBM, a bath of powders of the desired grain size of metal material by means of a beam of high speed electrons.

The powders of metal material, of the desired grain size, are deposited in successive layers in the desired place and in the desired, predefined sequence, and made to melt to form the layers, for example 11, 14 and 16, of metal material according to the present invention.

The EBM technique used in the step of making the metal support 30 may be replaced by an equivalent technique, such as for example the technique known as DMSLS (Direct Metal Selective Laser Sintering), in which the melting of the bath of powders is performed by means of a high power laser ray.

Once the metal support 30 has been obtained as described above, the method then proceeds to feed the plastic material into the cavities 12 of the solidarization layer 11 and, at the same time, to form the plastic insert 13.

Figure 8:
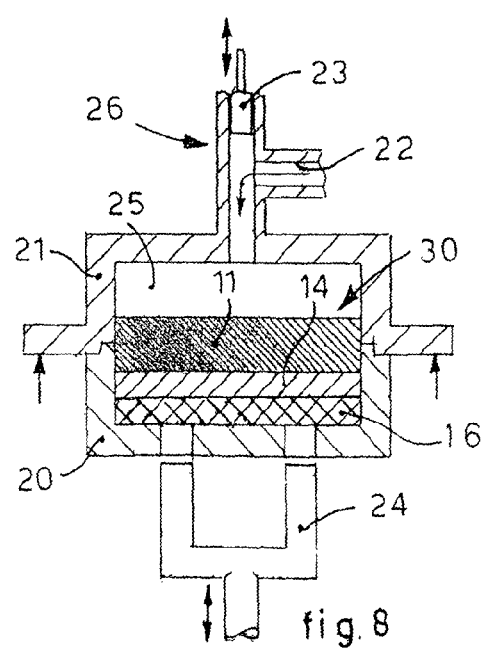
FIG. 8 is a schematic representation of a method for injecting the plastic material to achieve the invention.

FIG. 8 shows schematically a possible method of injecting the plastic material to make the plastic insert 13.

The metal support 30 is inserted into a mold 20 and is closed with a counter-mold 21 so as to form an injection chamber 25; the counter-mold 21 is equipped with an injection device 26 comprising an injection channel 22 to inject the plastic material and a pressurization mean 23. An extraction device 24 then allows to extract the prosthetic element 10 from the mold 20 once the injection is terminated and the plastic material cooled.

In particular the metal support 30 is inserted into the mold 20 obtained from the previous EBM production step and is closed by the counter-mold 21.

The plastic material is injected through the injection channel 22 and fills the injection chamber 25 and the cavities 12 of the solidarization layer 11, while the compact layer 14 contains the injection of the plastic, preventing it from penetrating and dispersing on the opposite side with respect to the side where the plastic material is injected.

The pressurization mean 23 promotes the penetration of the plastic material into the cavities 12 of the solidarization layer 11.

It is clear that modifications and/or additions of parts may be made to the integrated prosthetic element and relative method of production as described heretofore, without departing from the field and scope of the present invention.

The invention claimed is:

1. Integrated prosthetic element usable for bone implant operations as a femoral, shoulder or knee prosthesis, or as a bone filler or replacement, insert or shell, comprising at least a metal support and an insert made of plastic material coupled with at least a first surface of said metal support so as to define a wear surface, or insert, of adjustable thickness, said metal support comprising, on a side opposite said first surface, a second surface intended to be coupled with the bone part on which the prosthesis or bone replacement is installed, wherein said first surface comprises a solidarization layer, having cavities or holes which extend internally said first surface and are distributed in a substantially uniform manner and suitable for anchorage and solidarization of the plastic material that makes up the insert, while said second surface comprises a porous layer suitable to optimize the bone anchorage, wherein said first surface and said second surface are separated by a compact layer, and wherein the cavities or holes of the first surface have bigger shapes and sizes than the pores of the second surface, and wherein the metal support, with the solidarization layer, the compact layer and the porous layer are all obtained using either the Electron Beam Melting Technique (EBM), or a technique using a high power laser ray, from a powder material based on pure titanium, or an alloy thereof, or cobalt alloys, tantalum alloys or other suitable biocompatible alloy, and wherein said cavities or holes extend toward the inside of the solidarization layer and create at least undercuts, or have a series of open cavities intercommunicating and connected with each other.

2. Prosthetic element as in claim 1, wherein the plastic insert is at least partly obtained by feeding plastic material in its liquid or semi-liquid state into said cavities or holes of the solidarization layer made in the first surface.

3. Prosthetic element as in claim 1, wherein said metal support is made of titanium and/or cobalt and/or tantalum and/or their alloys.

4. Prosthetic element as in claim 1, wherein said plastic insert is made with a polymer material chosen from a group comprising polyether ether ketone, polycarbonate-urethane and polyethylene.

5. Prosthetic element as in claim 1, wherein said holes or cavities have width sizes varying in a range from 1200 to 2500 μm and more.

6. Prosthetic element as in claim 1, wherein the pores of the porous layer vary in a range from about 250 to about 1000 μm.

7. Prosthetic element as in claim 1, wherein said solidarization layer and said compact layer are made solid each other with a material based on pure titanium, or an alloy thereof, or cobalt alloys, tantalum alloys or other suitable biocompatible alloy.

8. Method to make an integrated prosthetic element usable for bone implant operations as a femoral, shoulder or knee prosthesis, or as a bone filler or replacement, insert or shell, comprising at least a metal support and an insert made of plastic material coupled with at least a first surface of said metal support so as to define a wear surface, or insert, of adjustable thickness, said metal support comprising, on the side opposite said first surface, a second surface intended to be coupled with the bone part on which the prosthesis or bone replacement is installed, the method comprising making the metal support so as to define at least an intermediate compact layer between said first and said second surface, wherein cavities or holes are made on said first surface which extend internally said first surface so as to define a solidarization layer, whereas on said second surface there is a surface porosity, wherein the cavities or holes of the first surface have bigger shapes and sizes than the pores of the second surface, and feeding, casting or injecting plastic material in a liquid or semi-liquid state, which penetrates into said cavities or holes of the solidarization layer until the compact layer is reached, wherein said cavities or holes extend inside and create at least undercuts, or are open cavities intercommunicating and connected with each other, and wherein said metal support and the relative first and second surface are made in a single process using either an EBM (Electron Beam Melting) technique or a technique using a high power laser ray, on a powder material selected between pure titanium, or an alloy thereof, or cobalt alloys, tantalum alloys or other suitable biocompatible alloy.

* * * * *